US009827187B2

(12) United States Patent
Gozu et al.

(10) Patent No.: US 9,827,187 B2
(45) Date of Patent: Nov. 28, 2017

(54) FILAGGRIN GENE EXPRESSION PROMOTER

(71) Applicant: Shiseido Company, Ltd., Chuo-ku, Tokyo (JP)

(72) Inventors: Yoko Gozu, Yokohama (JP); Shinichiro Haze, Yokohama (JP)

(73) Assignee: Shiseido Company, Ltd., Tokyo (JP)

( * ) Notice: Subject to any disclaimer, the term of this patent is extended or adjusted under 35 U.S.C. 154(b) by 39 days.

(21) Appl. No.: 14/419,715

(22) PCT Filed: Mar. 29, 2013

(86) PCT No.: PCT/JP2013/059674
§ 371 (c)(1),
(2) Date: Feb. 5, 2015

(87) PCT Pub. No.: WO2014/024518
PCT Pub. Date: Feb. 13, 2014

(65) Prior Publication Data
US 2015/0190336 A1    Jul. 9, 2015

(30) Foreign Application Priority Data

Aug. 10, 2012  (JP) ................................ 2012-178486

(51) Int. Cl.
| A61K 36/00 | (2006.01) |
| A61K 8/97 | (2017.01) |
| A61Q 19/00 | (2006.01) |
| A61K 31/235 | (2006.01) |
| A61K 31/245 | (2006.01) |
| A61K 36/23 | (2006.01) |
| A61K 36/53 | (2006.01) |
| A61K 36/73 | (2006.01) |
| A61K 8/44 | (2006.01) |
| A61K 8/92 | (2006.01) |
| A61K 36/758 | (2006.01) |
| A61K 36/14 | (2006.01) |
| A61K 36/185 | (2006.01) |
| A61K 36/67 | (2006.01) |
| A61K 9/00 | (2006.01) |
| A61K 47/10 | (2017.01) |
| A61K 47/14 | (2017.01) |
| A61K 9/06 | (2006.01) |
| A61K 47/44 | (2017.01) |
| A61K 9/20 | (2006.01) |
| A61K 9/50 | (2006.01) |
| A61K 8/37 | (2006.01) |
| A61K 8/41 | (2006.01) |
| A61K 8/49 | (2006.01) |

(52) U.S. Cl.
CPC ................ *A61K 8/97* (2013.01); *A61K 8/37* (2013.01); *A61K 8/411* (2013.01); *A61K 8/44* (2013.01); *A61K 8/445* (2013.01); *A61K 8/4926* (2013.01); *A61K 8/922* (2013.01); *A61K 9/0014* (2013.01); *A61K 9/06* (2013.01); *A61K 9/2018* (2013.01); *A61K 9/2068* (2013.01); *A61K 9/5042* (2013.01); *A61K 31/235* (2013.01); *A61K 31/245* (2013.01); *A61K 36/14* (2013.01); *A61K 36/185* (2013.01); *A61K 36/23* (2013.01); *A61K 36/53* (2013.01); *A61K 36/67* (2013.01); *A61K 36/73* (2013.01); *A61K 36/758* (2013.01); *A61K 47/10* (2013.01); *A61K 47/14* (2013.01); *A61K 47/44* (2013.01); *A61Q 19/00* (2013.01); *A61Q 19/007* (2013.01); *A61K 2800/70* (2013.01); *A61K 2800/74* (2013.01)

(58) Field of Classification Search
None
See application file for complete search history.

(56) References Cited

U.S. PATENT DOCUMENTS

| 2,170,185 A | 8/1939 | Carpenter |
| 2004/0044077 A1 | 3/2004 | Katagiri et al. |
| 2009/0041848 A1* | 2/2009 | Aimi ........................ A61K 8/64 424/489 |

(Continued)

FOREIGN PATENT DOCUMENTS

| JP | 2000302636 A | * | 10/2000 |
| JP | 2001-288045 A | | 10/2001 |
| JP | 2002-265327 A | | 9/2002 |

(Continued)

OTHER PUBLICATIONS

Casetti et al, Dermocosmetics for dry skin: A new role for botanical extracts. Skin Pharmacology and Physiology, (Sep. 2011) vol. 24, No. 6, pp. 289-293.*
Akashi et al., "Noninvasive method for assessing the human circadian clock using hair follicle cells," PNAS, Jul. 21, 2010, 107(35):15643-15648.
Morar et al., "Filaggrin Mutations in Children with Severe Atopic Dermatitis," Journal of Investigative Dermatology, Feb. 15, 2007, 127:1667-1672.

(Continued)

*Primary Examiner* — Qiuwen Mi
(74) *Attorney, Agent, or Firm* — Foley & Lardner LLP

(57) ABSTRACT

The present invention provides a novel substance that promotes expression of filaggrin gene involved in improvement of the moisture retention function of skin. The inventors of the present invention found that expression of filaggrin gene fluctuates rhythmically over a roughly 24 hour cycle, screened candidate substances based on the time at which expression reaches a maximum following addition of the candidate substance, and identified zanthoxylum extract, 3-(1'-piperidine)propionic acid, geranium oil, cypress oil, rose oil, galvanum oil, pepper oil, basil oil, methyl-o-toluate, methyl anthranilate and dimethyl anthranilate as filaggrin gene expression promoting agents.

20 Claims, 3 Drawing Sheets

(56) References Cited

U.S. PATENT DOCUMENTS

2010/0303872 A1  12/2010  Dumas et al.
2013/0022692 A1  1/2013  Gozu et al.

FOREIGN PATENT DOCUMENTS

| JP | 2002-363054 A | | 12/2002 |
|---|---|---|---|
| JP | 2003-306438 A | | 10/2003 |
| JP | 2006-016337 A | | 1/2006 |
| JP | 2007-217325 A | | 8/2007 |
| JP | 2010090113 A | * | 4/2010 |
| JP | 4540872 B2 | | 9/2010 |
| JP | 2011-168555 A | | 9/2011 |
| JP | 4768238 B2 | | 9/2011 |
| KR | 2009119340 A | * | 11/2009 |
| WO | WO 00/16752 A2 | | 3/2000 |
| WO | 02/053127 A1 | | 7/2002 |
| WO | WO 2011/122041 A1 | | 10/2011 |

OTHER PUBLICATIONS

Kim et al., "Enhancement of Keratinocyte Differentiation by Rose Absolute Oil," Annals of Dermatology, 2010, 22(3):255-261.

Kobayashi et al., "Regulatory Roles of BMAL1 in the skin functions," Biochemistry, Society Abstract CD, Poster 1P-1019, 2008, with English translation.

"Shiseido's new ingredient to protect skin from external stresses," premiumbeautynews.com, Apr. 4, 2009, http://www.premiumbeautynews.com/en/shiseido-s-new-intredient-to,776, 2 pages.

* cited by examiner

SEQUENCE LISTING

```
<160> NUMBER OF SEQ ID NOS: 8

<210> SEQ ID NO 1
<211> LENGTH: 20
<212> TYPE: DNA
<213> ORGANISM: Artificial Sequence
<220> FEATURE:
<223> OTHER INFORMATION: Primer

<400> SEQUENCE: 1
ctcaggcact gggcgcagac                                          20

<210> SEQ ID NO 2
<211> LENGTH: 20
<212> TYPE: DNA
<213> ORGANISM: Artificial Sequence
<220> FEATURE:
<223> OTHER INFORMATION: Primer

<400> SEQUENCE: 2
gcctgtccgt gggctgacac                                          20

<210> SEQ ID NO 3
<211> LENGTH: 20
<212> TYPE: DNA
<213> ORGANISM: Artificial Sequence
<220> FEATURE:
<223> OTHER INFORMATION: Primer

<400> SEQUENCE: 3
atgcggttac agcagcacca                                          20

<210> SEQ ID NO 4
<211> LENGTH: 20
<212> TYPE: DNA
<213> ORGANISM: Artificial Sequence
<220> FEATURE:
<223> OTHER INFORMATION: Primer

<400> SEQUENCE: 4
agggtccagg gctcacagaa                                          20
```

```
<210> SEQ ID NO 5
<211> LENGTH: 21
<212> TYPE: DNA
<213> ORGANISM: Artificial Sequence
<220> FEATURE:
<223> OTHER INFORMATION: Primer

<400> SEQUENCE: 5
ctccaggagg caagaagatt t                                                   21

<210> SEQ ID NO 6
<211> LENGTH: 21
<212> TYPE: DNA
<213> ORGANISM: Artificial Sequence
<220> FEATURE:
<223> OTHER INFORMATION: Primer

<400> SEQUENCE: 6
ctacttgatc cttggtcgtt g                                                   21

<210> SEQ ID NO 7
<211> LENGTH: 20
<212> TYPE: DNA
<213> ORGANISM: Artificial Sequence
<220> FEATURE:
<223> OTHER INFORMATION: Primer

<400> SEQUENCE: 7
ggcgacctgg aagtccaact                                                     20

<210> SEQ ID NO 8
<211> LENGTH: 20
<212> TYPE: DNA
<213> ORGANISM: Artificial Sequence
<220> FEATURE:
<223> OTHER INFORMATION: Primer

<400> SEQUENCE: 8
ccatcagcac cacagccttc                                                     20
```

FILAGGRIN GENE EXPRESSION PROMOTER

TECHNICAL FIELD

The present invention relates to a cosmetic and external skin preparation, and more particularly, to a promoting agent of the expression of filaggrin gene that is involved in improvement of the moisture retention function of skin.

BACKGROUND ART

The horny layer of the skin covers the living body whereby retaining moisture and providing a defense against invasion by foreign substances. The horny layer is composed of various substances such as proteins including keratin and filaggrin, and lipids, produced by epidermal keratinocytes. Filaggrin fulfills the important role of forming a structure referred to as a keratin pattern by assembling keratin fibers into layers. Filaggrin is produced from profilaggrin, a precursor encoded by filaggrin gene (FLG), accompanying with keratinization, and causes agglomeration of keratin fibers. Moreover, filaggrin is decomposed in the upper corneal layer, thereby it is transformed into low molecular weight peptides and amino acids referred to as natural moisturizing factors, and is involved in moisture retention and absorption of ultraviolet rays.

In this manner, filaggrin is intimately involved in the moisture retention and barrier function of the horny layer of the skin, and a decrease in filaggrin production is involved in the onset of dry skin diseases such as ichthyosis vulgaris, atopic dermatitis or senile xerosis (Non-Patent Document 1). In order to maintain healthy and attractive skin condition, the suitable production of filaggrin and a suitable cycle of continuous cornification are required.

In consideration of the above, research has been conducted on substances that promote filaggrin synthesis, and plant extracts such as wild thyme extract, clove extract, salvia extract, etc., are already known to be substances having effects that promote filaggrin synthesis (Patent Document 1). In addition, ectoin, which is accumulated by certain species of bacteria in order to regulate osmotic pressure, is known to inhibit decreases in filaggrin caused by drying (Patent Document 2).

PRIOR ART DOCUMENTS

Patent Documents

Patent Document 1: Japanese Patent No. 4768238
Patent Document 2: Japanese Patent No. 4540872

Non-Patent Documents

Non-Patent Document 1: Morar, N., et al., Filaggrin mutations in children with severe atopic dermatitis, Journal of Investigative Dermatology, 127, 1667-1672, 2007
Non-Patent Document 2: Akashi, M., et al., Noninvasive method for assessing the human circadian clock using hair follicle cells, Proc. Natl. Acad. Sci. USA, 107(35), 15643-15648, 2010

DISCLOSURE OF THE INVENTION

Problems to be Solved by the Invention

As was previously described, there is a strong desire among consumers for a substance having a more potent effect of promoting filaggrin synthesis, and development of a novel filaggrin synthesis promoting agent is currently sought. Thus, a problem to be solved by the present invention is to provide a novel substance that promotes filaggrin gene expression.

Means for Solving the Problems

As a result of conducting extensive studies on the expression of filaggrin gene, the inventors of the present invention surprisingly found for the first time that expression of filaggrin gene fluctuates rhythmically in a roughly 24 hour cycle. Thus, it was found that, in order to promote filaggrin production and maintain the skin in a healthy state, in addition to simply enhancing filaggrin production or inhibiting decreases in filaggrin production caused by drying as was carried out in the prior art, it is also important to promote production of filaggrin in consideration of this rhythmical property. Therefore, candidate substances were screened for filaggrin gene expression promoting action in consideration of this rhythmical property, thereby leading to completion of the filaggrin gene expression promoting agent of the present invention.

Zanthoxylum extract, 3-(1'-piperidine)propionic acid, geranium oil, cypress oil, rose oil, galvanum oil, pepper oil, basil oil, methyl-o-toluate, methyl anthranilate and dimethyl anthranilate, were selected by screening carried out by the inventors of the present invention as an agent having an effect of promoting filaggrin gene expression.

Thus, the present invention relates to a filaggrin gene expression promoting agent containing one or more substances selected from the group consisting of zanthoxylum extract, 3-(1'-piperidine) propionic acid, geranium oil, cypress oil, rose oil, galvanum oil, pepper oil, basil oil, methyl-o-toluate, methyl anthranilate and dimethyl anthranilate.

In another aspect of the present invention, the present invention relates to a method for promoting expression of filaggrin gene comprising administering one or more filaggrin gene expression promoting agents selected from the group consisting of zanthoxylum extract, 3-(1'-piperidine) propionic acid, geranium oil, cypress oil, rose oil, galvanum oil, pepper oil, basil oil, methyl-o-toluate, methyl anthranilate and dimethyl anthranilate to a subject requiring promotion of the expression of filaggrin gene.

In another aspect of the present invention, the present invention relates to use of one or more substances selected from the group consisting of zanthoxylum extract, 3-(1'-piperidine)propionic acid, geranium oil, cypress oil, rose oil, galvanum oil, pepper oil, basil oil, methyl-o-toluate, methyl anthranilate and dimethyl anthranilate for preparing a filaggrin gene expression promoting agent.

Moreover, the present invention relates to a method for promoting expression of filaggrin gene or a cosmetic method comprising administering a filaggrin gene expression promoting agent at a time at which the biological rhythm of filaggrin gene expression level and the rhythm of the filaggrin gene expression level resulting from administration of the filaggrin gene expression promoting agent are synchronous, based on the finding that expression of filaggrin gene fluctuates rhythmically in a roughly 24 hour cycle. Moreover, the present invention also relates to a filaggrin gene expression promoting agent that is used such that the filaggrin gene expression promoting agent is administered at a time at which the biological rhythm of filaggrin gene expression level and the rhythm of the filaggrin gene expression level resulting from administration of the filaggrin gene expression promoting agent are synchronous, and to a filaggrin gene expression promoting agent that is used such that the filaggrin gene expression promoting agent is administered at a time at which the rhythm of the filaggrin gene expression level is restored by administration of the filaggrin gene expression promoting agent in a subject in which the biological rhythm of filaggrin gene expression level is disturbed.

Effects of the Invention

The filaggrin gene expression promoting agent according to the present invention has at least one of the effects listed below:
promotion of the expression of filaggrin gene;
enhancement of the skin's barrier function; and
moisture retention.

BEST MODE FOR CARRYING OUT THE INVENTION

Figure 1:
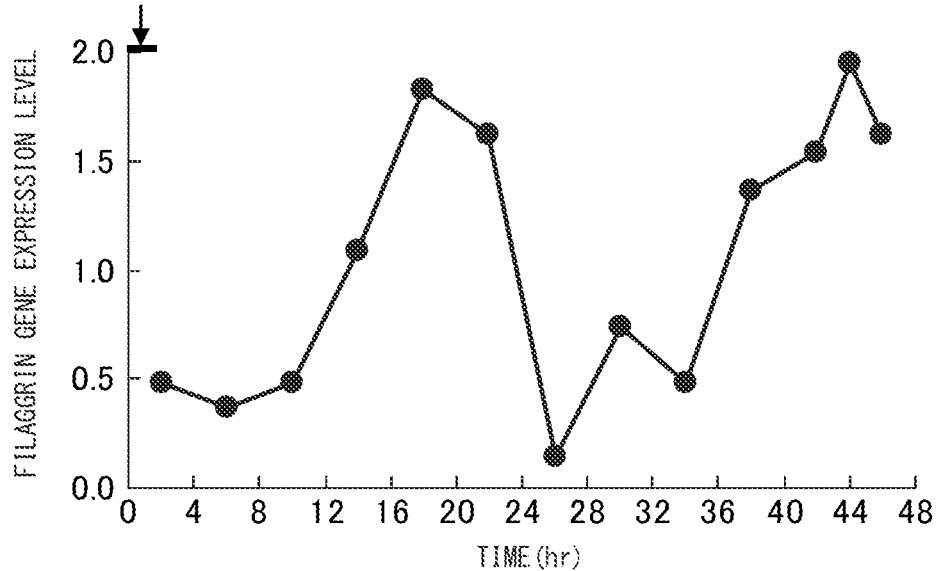
FIG. 1 is a graph indicating the rhythmic 24-hour fluctuations of filaggrin gene expression in cultured keratinocytes temporarily cultured in medium containing cortisol.

The present invention relates to a filaggrin gene expression promoting agent comprising one or more substances selected from the group consisting of zanthoxylum extract, 3-(1'-piperidine)propionic acid, geranium oil, cypress oil, rose oil, galvanum oil, pepper oil, basil oil, methyl-o-toluate, methyl anthranilate and dimethyl anthranilate. The substances exemplified above may be used alone for the filaggrin gene expression promoting agent or may be used in combination. More preferably, zanthoxylum extract is selected for the filaggrin gene expression promoting agent of the present invention. Even more preferably, a combination of zanthoxylum extract and 3-(1'-piperidine)propionic acid is selected for the filaggrin gene expression promoting agent.

In another aspect thereof, the filaggrin gene expression promoting agent of the present invention further comprises another previously known pharmaceutical agent having a filaggrin gene expression promoting effect such as wild thyme extract, clove extract, salvia extract or ectoin.

The filaggrin gene expression promoting agent of the present invention is able to promote filaggrin synthesis by promoting expression of filaggrin gene. More specifically, profilaggrin is synthesized through the expression of filaggrin gene, is subjected to phosphorylation, and then is subjected to dephosphorylation and hydrolysis by peptidyl arginine deiminase during keratinization, thereby filaggrin is synthesized. Thus, a filaggrin gene expression promoting agent is also referred to as a profilaggrin gene expression promoting agent, and may also be a filaggrin synthesis promoting agent that promotes synthesis of filaggrin by promoting expression of filaggrin gene.

The filaggrin gene expression promoting agent of the present invention promotes filaggrin synthesis and further brings about an increase in amino acids that are the main components of natural moisturizing factors (NMF) produced from the decomposition of filaggrin. Thus, the filaggrin gene expression promoting agent of the present invention may also be a natural moisturizing factor enhancing agent, a moisturizing agent, or skin barrier function enhancing agent, since it enhances natural moisturizing factors, and is incorporated in a cosmetic. Moreover, dry skin and dry skin diseases such as senile xerosis, atopic dermatitis or ichthyosis vulgaris can be treated by the filaggrin gene expression promoting agent or method for promoting expression of filaggrin gene of the present invention.

In one aspect of the present invention, the filaggrin gene expression promoting agent of the present invention may be administered through an arbitrary route, and may be administered either orally or parenterally (such as by transcutaneous, transmucosal, subcutaneous, intravenous, intraperitoneal, transpulmonary or intramuscular administration). In the case of oral administration, the filaggrin gene expression promoting agent may be administered by formulating into a tablet or capsule and the like, or may be administered as a drink or supplement. In the case of transcutaneous administration, it may be incorporated in a cosmetic or external skin preparation and may be administered by applying to the skin. In the case of transpulmonary administration, the filaggrin gene expression promoting agent may be administered by inhaling a mist of a solution obtained by the dissolution thereof or inhaling after vaporizing, and may be administered in the form of aroma therapy, for example. The filaggrin gene expression promoting agent is preferably administered transcutaneously from the viewpoint of promoting expression of filaggrin gene in epidermal cells.

The filaggrin gene expression promoting agent of the present invention is administered to not only subjects requiring promotion of expression of filaggrin gene, such as subjects desiring enhancement of moisturizing and the skin's barrier function, but also to subjects in which the biological rhythm of filaggrin gene expression level is disturbed. The subjects requiring promotion of filaggrin gene expression include, for example, subjects suffering from dry skiun, dry skin diseases such as senile xerosis, atopic dermatitis or ichthyosis vulgaris.

The filaggrin gene expression promoting agent of the present invention refers to a cosmetic, pharmaceutical, quasi-drug or product applied to the skin, and therefore the form thereof can be any of a wide range of forms such as an aqueous solution type, solubilized type, emulsified type, powdered type, gel type, ointment type, cream, water-oil two-layer type or water-oil-powder three-layer type. Examples of cosmetics to which the present invention can be applied include skin lotions, creams, milky lotions, gel, beauty essence, ointments, packs, bath additives, body soaps, shampoos, rinses and foundations. In the case of a pharmaceutical or quasi-drug, the present invention can be applied in various forms such as ointments or creams.

The cosmetic and/or external skin preparation of the present invention may also contain active ingredients and/or excipients commonly used in the production of cosmetics and/or external skin preparations, and examples thereof include bases such as water, alcohol, glycerin or hyaluronic acid, surfactants, moisturizers, thickeners, pH adjusters, UV absorbing agent, stabilizers, antimicrobials, fragrances and so on.

As shown in FIG. 1, expression of filaggrin gene rhythmically fluctuates over a roughly 24 hour cycle in a cultured cell system of keratinocytes, and this rhythm is thought to be equivalent to circadian rhythm. Circadian rhythm is a cyclical rhythm having a roughly 24 hour cycle that is controlled by a feedback loop composed of clock proteins such as CLOCK, BMAL1, CRY or PER, and is known to have an effect on various physiological phenomena such as sleep/awakedness, hormone secretion, body temperature and cell cycle in the body.

Since expression levels of filaggrin gene are thought to fluctuate in line with circadian rhythm in vivo, the filaggrin gene expression promoting agent of the present invention can promote fillaggrin synthesis more effectively by administering the filaggrin gene expression promoting agent in conformance with circadian rhythm, and more specifically, by administering so as to synchronize with the time of the maximum or minimum expression level of filaggrin expression.

In another aspect of the present invention, the present invention relates to a cosmetic method comprising administering a filaggrin gene expression promoting agent at a time at which the biological rhythm of filaggrin gene expression level and the rhythm of the filaggrin gene expression level resulting from administration of the filaggrin gene expression promoting agent are synchronous. In the present invention, a cosmetic method refers not only to a method carried out by an individual, but also refers to that provided as a cosmetic formula in accordance with customer preferences when providing beauty products as well as that provided by a cosmetic salesperson or esthetician other than a physician.

In another aspect of the present invention, the present invention relates to a filaggrin gene expression promoting agent that is used so as to be administered at a time at which the biological rhythm of filaggrin gene expression level and the rhythm of the filaggrin gene expression level resulting from administration of the filaggrin gene expression promoting agent are synchronous.

In still another aspect, the present invention relates to a method for promoting expression of filaggrin gene that comprises administering a filaggrin gene expression promoting agent at a time at which the biological rhythm of filaggrin gene expression level and the rhythm of the filaggrin gene expression level resulting from administration of the filaggrin gene expression promoting agent are synchronous in a subject requiring promotion of filaggrin gene expression. This method for promoting expression of filaggrin gene is a method for treating dry skin and dry skin diseases such as senile xerosis, atopic dermatitis or ichthyosis vulgaris.

Synchronous administration refers to administering such that the peak of the biological rhythm of filaggrin gene expression level and the peak of fluctuations in filaggrin gene expression level resulting from administration of the filaggrin gene expression promoting agent overlap, and refers to the administration of filaggrin gene expression promoting agent at 16 hours to 22 hours, more specifically 17 hours to 21 hours, and even more specifically 18 hours to 20 hours, prior to the time filaggrin gene expression level reaches a maximum.

In actuality, since the peak of filaggrin gene expression in humans is estimated to be from about 5:00 AM to 11:00 AM, more specifically from about 6:00 AM to 10:00 AM, and even more specifically from about 7:00 AM to 9:00 AM, the filaggrin gene expression promoting agent is thought to be preferably administered, for example, at 16 hours to 22 hours, more specifically 17 hours to 21 hours, and even more specifically 18 hours to 20 hours prior thereto. For example, the filaggrin gene expression promoting agent is thought to be preferably administered between the times of about 7:00 AM to 1:00 PM to about 1:00 PM to 7:00 PM corresponding to 16 hours to 22 hours prior to the peak of filaggrin gene expression.

As was clearly determined in the present invention, filaggrin is expressed in accordance with the rhythm of the body's internal clock, and when this rhythm of the body's internal clock is disturbed by some form of cause such as aging, stress, inadequate sleep or disturbances in daily rhythm, the rhythm of filaggrin expression is thought to shift correspondingly or the expression level thereof is thought to decrease. Thus, by administering the filaggrin gene expression promoting agent of the present invention at the proper timing, restoration of the expression rhythm of filaggrin can be expected to be restored or expression levels thereof can be expected to increase. Therefore, in another aspect of the present invention, the filaggrin gene expression promoting agent of the present invention administered at the proper timing can be used as an agent for improving or restoring the expression level of filaggrin. With respect to this proper timing, since the peak of filaggrin gene expression in humans is estimated to be from about 5:00 AM to 11:00 AM, more specifically from about 6:00 AM to 10:00 AM, and even more specifically from about 7:00 AM to 9:00 AM, the filaggrin gene expression promoting agent is thought to be preferably administered 16 hours to 22 hours, more specifically 17 hours to 21 hours, and even more specifically 18 hours to 20 hours prior thereto.

Since the expression of filaggrin gene fluctuates cyclically roughly every 24 hours, when screening filaggrin gene expression promoting agents, by comparing filaggrin gene expression level during the time of minimum expression roughly 0 hours to 10 hours, preferably 2 hours to 8 hours and more preferably 4 hours to 6 hours after administering a candidate pharmaceutical agent to cultured cells such as cultured keratinocytes, with filaggrin gene expression level during the time of maximum expression roughly 16 hours to 22 hours, preferably 17 hours to 21 hours and more preferably 18 hours to 20 hours after administering the candidate pharmaceutical agent, filaggrin gene expression promoting agents can be screened more accurately. In still another aspect, filaggrin gene expression promoting agents can be screened by using filaggrin gene expression level during the time of maximum expression as an indicator. In still another aspect, filaggrin gene expression promoting agents can be screened by determining fillaglin gene expression level at the time of maximum expression after the second cycle, such as at 40 hours to 48 hours or at 64 hours to 72 hours, as an indicator.

Geranium oil, which is one of the pharmaceutical agents that demonstrates the effect of the filaggrin gene expression promoting agent of the present invention, is an essential oil derived from the entire plant of a plant belonging to the genus *Pelargonium* such as *Pelargonium graveolens*, and examples thereof include essential oils obtained by steam distillation of the entire plant of plants belonging to the aforementioned genus *Pelargonium*.

Cypress oil, which is one of the pharmaceutical agents that demonstrates the effect of the filaggrin gene expression promoting agent of the present invention, is an essential oil derived from *Cupressus sempervirens*, and examples thereof include essential oils obtained by steam distillation of the branches and leaves of Cypress plants.

Rose oil, which is one of the pharmaceutical agents that demonstrates the effect of the filaggrin gene expression promoting agent of the present invention, is an essential oil derived from the flower petals of a plant belonging to the genus *Rosa* such as *Rosa centifolia* L. or *Rosa damascene* Mill., and examples thereof include essential oils obtained by steam distillation of the flower petals of plants belonging to the aforementioned genus *Rosa*.

Galvanum oil, which is one of the pharmaceutical agents that demonstrates the effect of the filaggrin gene expression promoting agent of the present invention, is an essential oil derived from a rubbery exudate that seeps from the leaves and buds of *Ferula galbaniflua* of the family Umbelliferae and related species thereof, and examples thereof include essential oils obtained by steam distillation.

Pepper oil, which is one of the pharmaceutical agents that demonstrates the effect of the filaggrin gene expression promoting agent of the present invention, is an essential oil derived from the berries of pepper (*Piper nigrum* L.), a perennial plant belonging to the family Piperaceae, and examples thereof include essential oils obtained by steam distillation of the berries thereof.

Basil oil, which is one of the pharmaceutical agents that demonstrates the effect of the filaggrin gene expression promoting agent of the present invention, is an essential oil derived from the entire above ground portion of basil (*Ocimum basilicum* L.), an annual belonging to the family Labiatae, and examples thereof include essential oils collected by steam distillation of the entire above ground portion thereof.

*Zanthoxylum* extract, which is one of the pharmaceutical agents that demonstrates the effect of the filaggrin gene expression promoting agent of the present invention, is an extract of *Zanthoxylum piperitum* belonging to the genus *Zanthoxylum* of the family Rutaceae. The zanthoxylum extract of the present invention can be obtained in accordance with ordinary methods, such as by immersing or heating to reflux a leaf, stem, root, flower, fruit, bark, stone or the entire plant of zanthoxylum, or mixture thereof, with an extraction solvent followed by filtration and concentration. Any extraction solvent can be used provided it is ordinarily used for extraction, and examples of extraction solvents include water, alcohols such as methanol, ethanol, propylene glycol, 1,3-butylene glycol or glycerin, aqueous alcohols, and organic solvents such as chloroform, dichloroethane, carbon tetrachloride, acetone, ethyl acetate or hexane, and these can each be used alone or used in combination. In addition, extracts obtained by extracting with the aforementioned solvents can be used directly, or concentrated extracts can be adsorbed with a porous polymer column (such as the Amberlite XAD-2) after having removed impurities using an adsorption method or ion exchange resin and the like, followed by eluting with methanol or ethanol and concentrating prior to use. In addition, an extract obtained by extracting using a partition method, such as a mixture of water and ethyl acetate, can also be used. The extract is preferably extracted using a lowly irritative solvent such as water, 1,3-butylene glycol or glycerin from the viewpoint of using in a cosmetic or pharmaceutical such as an external skin preparation that is applied directly to the skin.

An essential oil refers to a mixture of insoluble to poorly soluble organic compounds in water contained in a plant, typically contains volatile organic compounds, and may be aromatic according to the raw material used. Since an essential oil is a mixture of insoluble to poorly soluble organic compounds in water contained in a plant, it is typically formed by steam distillation. However, in the present invention, an essential oil is not intended to be limited to a mixture formed by steam distillation, but rather is intended to include water-insoluble or poorly soluble extracts that use a portion of a plant body as raw material and are extracted with an organic solvent. Namely, in the present invention, an "essential oil" refers to a mixture of organic compounds specified according to the plant used as raw material (and the site thereof depending on the case) that demonstrate the desired effect of the present invention, namely action that promotes expression of filaggrin gene.

Methyl o-toluate (also known as methyl 2-methylbenzoate), which is one of the pharmaceutical agents that demonstrates the effect of the filaggrin gene expression promoting agent of the present invention, is a compound represented by the molecular formula $C_9H_{10}O_2$, has a molecular weight of 150.17, and is a liquid at normal temperature.

Methyl anthranilate (also known as methyl 2-aminobenzoate), which is one of the pharmaceutical agents that demonstrates the effect of the filaggrin gene expression promoting agent of the present invention, is a compound represented by the molecular formula $C_8H_9O_2N$, has a molecular weight of 151.17, and is a liquid at normal temperature.

Dimethyl anthranilate (also known as 2-methyl aminomethylbenzoate), which is one of the pharmaceutical agents that demonstrates the effect of the filaggrin gene expression promoting agent of the present invention, is a compound represented by the molecular formula $C_9H_{11}O_2N$, has a molecular weight of 165.20, and is a liquid at normal temperature.

3-(1'-piperidine)propionic acid (1PP), which is one of the pharmaceutical agents that demonstrates the effect of the filaggrin gene expression promoting agent of the present invention, is a compound represented by the molecular formula $C_8H_{15}NO_2$, has a molecular weight of 157.21, and is a solid at normal temperature.

EXAMPLES

Example 1

Examination of Filaggrin Gene Expression in Human Skin-Derived Keratinocytes

Commercially available normal adult skin-derived keratinocytes (Cellntec AG) were disseminated in a culture plate to a concentration of $3 \times 10^3$ cells/cm² followed by culturing in epithelial cell medium (CnT-BM.1, Cellntec AG) at 37° in a 5% $CO_2$ atmosphere. Three days later, the medium was replaced with medium containing cortisol at 50 ng/mL followed by synchronously culturing at 37° C. and 5% $CO_2$. Two hours later, culturing was continued after replacing the medium with ordinary medium after which the cells were collected over time. RNA was extracted from the collected cells using a commercially available RNA extraction-cDNA synthesis kit (FastLane Cell cDNA Kit, Qiagen N.V.) to prepare cDNA. Filaggrin expression levels were measured by quantitative PCR (QPCR) using this cDNA. Expression levels of clock genes PER3 and BMAL1 were measured simultaneously and compared with the expression rhythm of filaggrin gene. A commercially available QPCR reagent kit (Brilliant III Ultra-Fast SYBR Green QPCR Kit, Agilent Technologies Inc.) and QPCR measurement system (MX-3000P Real-time Quantitative PCR System, Agilent Technologies Inc.) were used for QPCR. The expression level of a housekeeping gene in the form of RPLP0 gene was quantified for use as an internal standard, and the relative expression level with respect to PLP0 was calculated and used as the expression level of filaggrin gene. Commercially available filaggrin and PER3, BMAL1 and RPLP0 primers (Perfect Real Time Primer, Takara Bio Inc.) were used for the PCR primers. The sequences of the primers used are shown in Table 1.

TABLE 1

Primer Sequences

5'→3'

| | | |
|---|---|---|
| Filaggrin | Forward | CTCAGGCACTGGGCGCAGAC |
| | Reverse | GCCTGTCCGTGGGCTGACAC |
| PER3 | Forward | ATGCGGTTACAGCAGCACCA |
| | Reverse | AGGGTCCAGGGCTCACAGAA |
| BMAL1 | Forward | CTCCAGGAGGCAAGAAGATTT |
| | Reverse | CTACTTGATCCTTGGTCGTTG |
| RPLP0 | Forward | GGCGACCTGGAAGTCCAACT |
| | Reverse | CCATCAGCACCACAGCCTTC |

Figure 2:
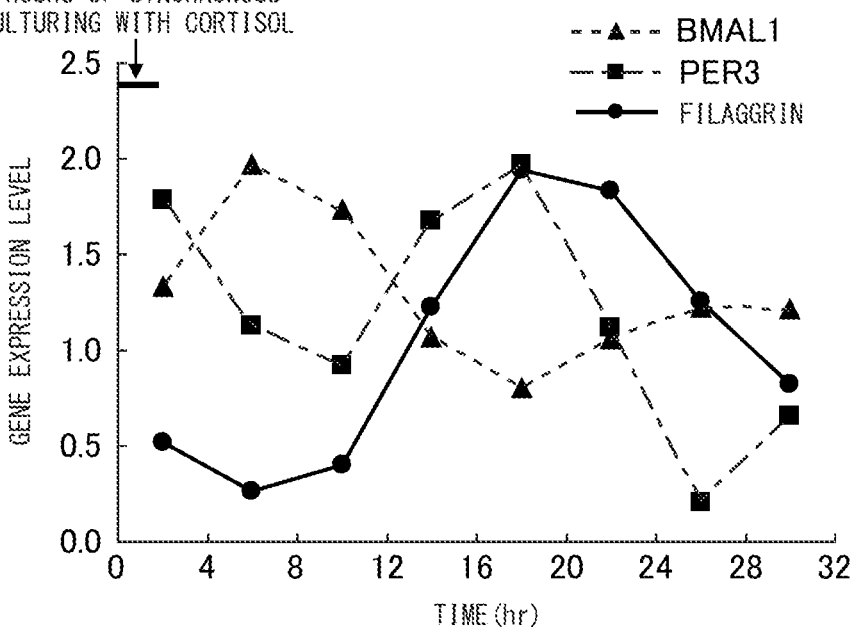
FIG. 2 is a graph indicating the rhythmic 24-hour fluctuations in the expression levels of filaggrin gene and clock genes BMAL1 and PER3 in cultured keratinocytes temporarily cultured in medium containing cortisol.

The results are shown in FIGS. 1 and 2. Expression of filaggrin gene was found to fluctuate rhythmically over a roughly 24 hour cycle in a cultured cell system of keratinocytes, and in the keratinocytes, the expression level of filaggrin gene was found to reach a maximum about 18 hours after the start of synchronous culturing with cortisol. This rhythm is thought to be equivalent to circadian rhythm. In addition, the expression rhythm of filaggrin gene was in the same phase as the expression rhythm of clock gene PER3 but was in the opposite phase from BMAL1. In actuality, the expression peak of PER3 in humans has been reported to be from 5:00 AM to 11:00 AM, more specifically from 6:00 AM to 10:00 AM and even more specifically from 7:00 AM to 9:00 AM (Non-Patent Document 2). Based on a comparison between the peak expression time of PER3 and the peak expression time of filaggrin gene as shown in FIG. 2, the expression peak of filaggrin gene and the expression peak of PER3 in humans are presumed to be roughly the same.

Example 2

Screening Pharmaceutical Agents that Promote Filaggrin Gene Expression

Commercially available normal adult skin-derived keratinocytes (Cellntec AG) were disseminated in a culture plate to a concentration of $3 \times 10^3$ cells/cm$^2$ followed by culturing in epithelial cell medium (CnT-BM.1, Cellntec AG) at 37° in a 5% $CO_2$ atmosphere. Three days later, the medium was replaced with medium containing each of the candidate pharmaceutical agents at a concentration of 1% followed by continuing culturing at 37° C. and 5% $CO_2$ and collecting the cells after 2 hours and after 18 hours. The candidate pharmaceutical agents added to the medium consisted of zanthoxylum extract (Maruzen Pharmaceuticals Co., Ltd.), geranium oil (Koei Kogyo Co., Ltd.), cypress oil (Bioland Co., Ltd.), rose oil (Bioland Co., Ltd.), galvanum oil (Bioland Co., Ltd.), pepper oil (Bioland Co., Ltd.), basil oil (Bioland Co., Ltd.), methyl-o-toluate (Aldrich Inc.), methyl anthranilate (Tokyo Chemical Industry Co., Ltd.), dimethyl anthranilate (Tokyo Chemical Industry Co., Ltd.), clove bud caryophyllata oil (Bioland Co., Ltd.) and arnica oil (Koei Kogyo Co., Ltd.). The absence of addition of pharmaceutical agent was used as a negative control, and cortisol (concentration in medium: 50 ng/mL) was used as a positive control.

RNA was extracted from the collected cells using a commercially available RNA extraction-cDNA synthesis kit (FastLane Cell cDNA Kit, Qiagen N.V.) to prepare cDNA. Filaggrin expression levels were measured by quantitative PCR (QPCR) using this cDNA. Expression levels of clock genes PER3 and BMAL1 were measured simultaneously and compared with the expression rhythm of filaggrin gene. A commercially available QPCR reagent kit (Brilliant III Ultra-Fast SYBR Green QPCR Kit, Agilent Technologies Inc.) and QPCR measurement system (MX-3000P Real-time Quantitative PCR System, Agilent Technologies Inc.) were used for QPCR. The expression level of a housekeeping gene in the form of RPLP0 gene was quantified for use as an internal standard, and the relative expression level with respect to PLP0 was calculated and used as the expression level of filaggrin gene. The primer sequences shown in Table 1 were used for the sequences of the PCR primers.

Figure 3:
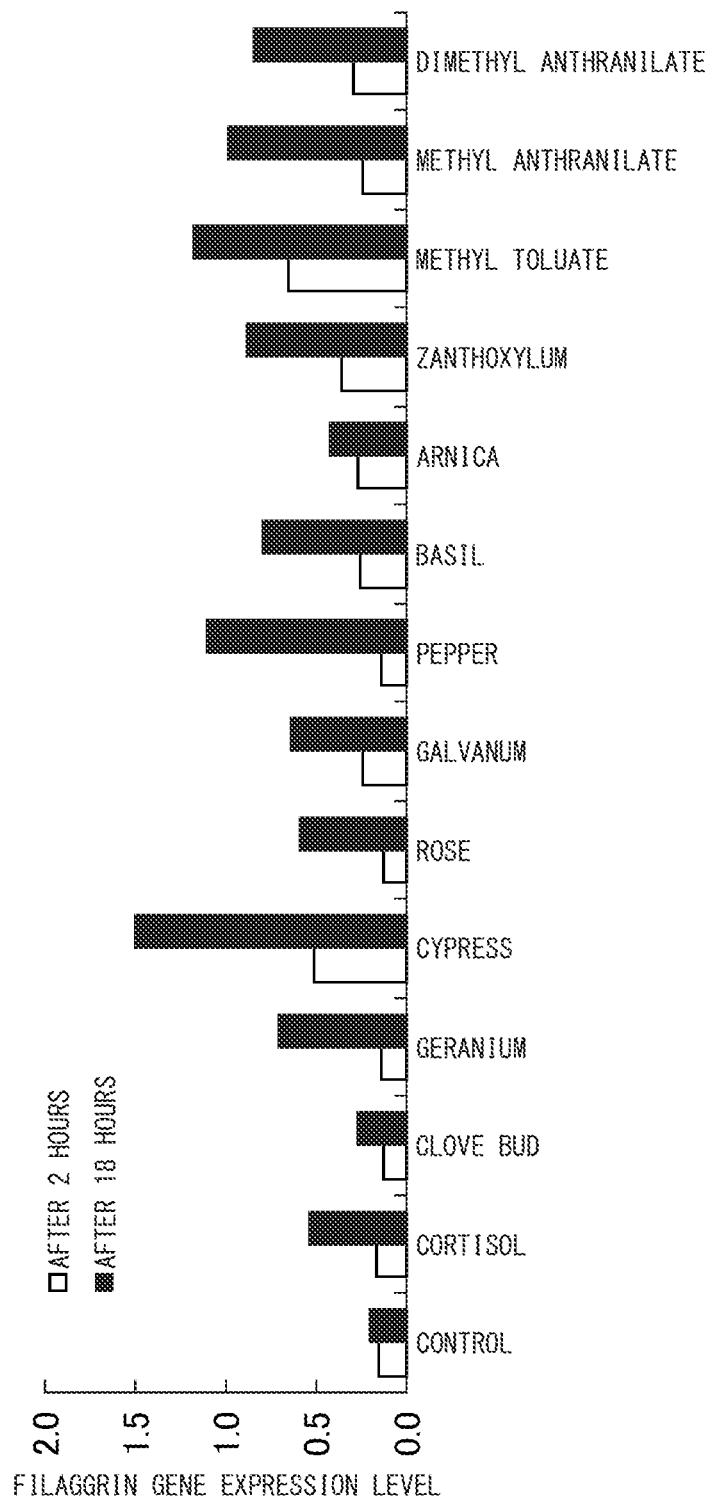
FIG. 3 is a bar graph indicating the results for filaggrin gene expression promoting action of candidate pharmaceutical agents.

FIG. 3 shows expression levels of filaggrin gene at 2 hours and 18 hours after addition of each of the candidate pharmaceutical agents. *Zanthoxylum* extract, geranium oil, cypress oil, rose oil, galvanum oil, pepper oil, basil oil, methyl-o-toluate, methyl anthranilate and dimethyl anthranilate were shown to promote expression of filaggrin gene after 18 hours in comparison with the negative control. On the other hand, although expression of filaggrin gene increased after 18 hours in the case of clove bud and arnica, there were no significant differences between the amounts of those increases and the control.

Example 3

Pharmaceutical Agents Promoting Expression of Filaggrin Gene

Commercially available normal adult skin-derived keratinocytes (Cellntec AG) were disseminated in a culture plate to a concentration of $3 \times 10^3$ cells/cm$^2$ followed by culturing in epithelial cell medium (CnT-BM.1, Cellntec AG) at 37° in a 5% $CO_2$ atmosphere. Three days later, the medium was replaced with medium containing 3-(1'-piperidine)propionic acid (1PP, Yuki Gousei Kogyo Co., Ltd.) at a concentration of 0.1%, medium containing zanthoxylum extract at a concentration of 0.1%, and medium containing both 1PP at 0.1% and zanthoxylum extract at 0.1%, followed by continuing culturing at 37° C. and 5% $CO_2$ and collecting the cells after 18 hours. The absence of addition of pharmaceutical agent was used as a control.

Figure 4:
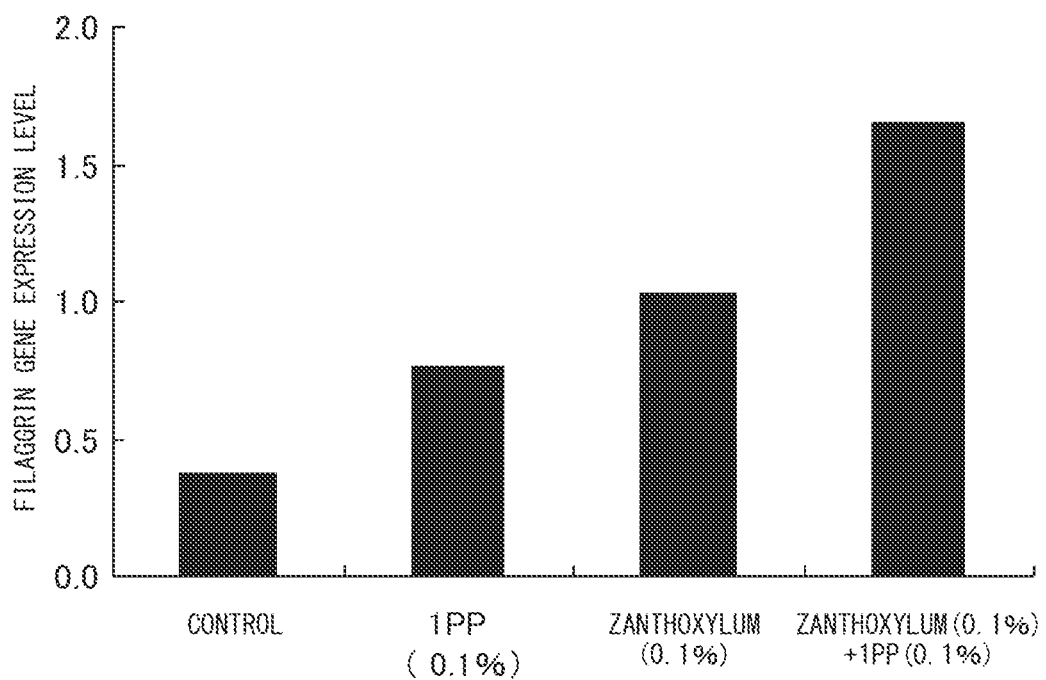
FIG. 4 is a bar graph indicating the results for filaggrin gene expression promoting action in the case of using 3-(1'-piperidine)propionic acid, zanthoxylum extract and a combination thereof as candidate pharmaceutical agents.

RNA was extracted from the collected cells using a commercially available RNA extraction-cDNA synthesis kit (FastLane Cell cDNA Kit, Qiagen N.V.) to prepare cDNA. Filaggrin expression levels were measured by quantitative PCR (QPCR) using this cDNA. A commercially available QPCR reagent kit (Brilliant III Ultra-Fast SYBR Green QPCR Kit, Agilent Technologies Inc.) and QPCR measurement system (MX-3000P Real-time Quantitative PCR System, Agilent Technologies Inc.) were used for QPCR. The expression level of a housekeeping gene in the form of RPLP0 gene was quantified for use as an internal standard, and the relative expression level with respect to PLP0 was calculated and used as the expression level of filaggrin gene. The primer sequences shown in Table 1 were used for the sequences of the PCR primers. The results are shown in FIG. 4. 1PP at a concentration of 0.1% demonstrated an effect of promoting filaggrin gene expression that was comparable to that of zanthoxylum extract at 0.1%, while the combined use of zanthoxylum extract and 1PP further promoted expression of filaggrin gene.

Formulation Examples

Although the following indicates formulation examples of the filaggrin gene expression promoting agent of the present invention, working of the present invention is not limited to the following examples.

Fragrance

| | |
|---|---|
| (1) Alcohol | 75.0 |
| (2) Purified water | Balance |
| (3) Dipropylene glycol | 5.0 |
| (4) Filaggrin gene expression promoting agent of present invention: Rose oil | 10.0 |
| (5) Antioxdiant | 8.0 |
| (6) Pigment | As suitable |
| (7) Ultraviolet absorber | As suitable |

Room Fragrance

| | |
|---|---|
| (1) Alcohol | 80.0 |
| (2) Purified water | Balance |
| (3) Antioxidant | 5.0 |
| (4) Filaggrin gene expression promoting agent of present invention: Cypress oil | 3.0 |
| (5) 3-methyl-3-methoxybutanol | 5.0 |
| (6) Dibenzylidene sorbitol | 5.0 |

Incense

| | |
|---|---|
| (1) Tabunoki powder | 75.5 |
| (2) Sodium benzoate | 15.5 |
| (3) Filaggrim gene expression promoting agent of present invention: Galvanum oil | 5.0 |
| (4) *Eucalyptus* oil | 1.0 |
| (5) Purified water | Balance |

Bath Additive

| | |
|---|---|
| (1) Sodium sulfate | 45.0 |
| (2) Sodium bicarbonate | 45.0 |
| (3) Lavender oil | 9.0 |
| (4) Filaggrin gene expression promoting agent of present invention: Methyl anthranilate | 1.0 |

Massage Gel

| | |
|---|---|
| (1) Erythritol | 2.0 |
| (2) Caffeine | 5.0 |
| (3) *Phellodendron* bark extract | 3.0 |
| (4) Glycerin | 50.0 |
| (5) Carboxyvinyl polymer | 0.4 |
| (6) Polyethylene glycol 400 | 30.0 |
| (7) Trisodium edetate | 0.1 |
| (8) Polyoxylene(10)-methylpolysiloxane copolymer | 2.0 |
| (9) Squalane | 1.0 |
| (10) Potassium hydroxide | 0.15 |
| (11) Filaggrin gene expression promoting agent of present invention: Geranium oil | 1.0 |

Massage Cream

| | |
|---|---|
| (1) Solid paraffin | 5.0 |
| (2) Beeswax | 10.0 |
| (3) Vaseline | 15.0 |
| (4) Liquid paraffin | 41.0 |
| (5) 1,3-butylene glycol | 4.0 |
| (6) Glycerin monostearate | 2.0 |
| (7) POE(20) sorbitan monolaurate | 2.0 |
| (8) Borax | 0.2 |
| (9) Caffeine | 2.0 |
| (10) Antiseptic | As suitable |
| (11) Antioxidant | As suitable |
| (12) Filaggrin gene expression promoting agent of present invention: *Zanthoxylum* extract | 1.0 |
| (13) Purified water | Balance |

Aromatic Fibers

Microcapsules containing the filaggrin gene expression promoting agent of the present invention (particle diameter: 50 μm or less, ratio of pharmaceutical agent in microcapsule: 50% by weight) were added to and mixed with a cuprammonium cellulose solution (cellulose concentration: 10% by weight, ammonium concentration: 7% by weight, copper concentration: 3.6% by weight) within the range of 1% to 20% based on the weight of cellulose followed by spinning into fibers in accordance with an ordinary wet spinning method and going through a scouring step and drying step to obtain aromatic fibers.

Granules

| | |
|---|---|
| (1) Sucralose | 0.1 |
| (2) Filaggrin gene expression promoting agent of present invention: *Zanthoxylum* extract | 0.1 |
| (3) Flavoring agent | 5.0 |
| (4) Excipient (Ceolus) | 10.0 |
| (5) Maltitol | Balance |

Tablets (Chewable)

| | |
|---|---|
| (1) Inositol | 11.0 |
| (2) Maltitol | 21.0 |
| (3) Sucrose | 0.5 |
| (4) Salmon milt extract (DNA Na) | 0.1 |
| (5) Yeast extract | 0.1 |
| (6) Filaggrin gene expression promoting agent of present invention: Basil oil | 0.1 |
| (7) Flavoring agent | 5.0 |
| (8) Excipient | Balance |

Tablets

| | |
|---|---|
| (1) Lubricant (such as sucrose fatty acid ester) | 1.0 |
| (2) Aqueous gum arabic solution (5%) | 2.0 |
| (3) Acidifier | 1.0 |
| (4) Colorant | As suitable |
| (5) Filaggrin gene expression promoting agent of present invention: Pepper oil | 0.1 |
| (6) Sugar (such as powdered sugar or sorbitol) | Balance |

Candy

| | |
|---|---|
| (1) Sugar | 50.0 |
| (2) Starch syrup | 47.95 |
| (3) Organic acid | 2.0 |
| (4) Filaggrin gene expression promoting agent of present invention: Rose oil | 0.05 |

Gum

| | |
|---|---|
| (1) Sugar | 43.0 |
| (2) Gum base | 30.95 |
| (3) Glucose | 10.0 |
| (4) Starch syrup | 16.0 |
| (5) Filaggrin gene expression promoting agent of present invention: Basil oil | 0.05 |

Cleansing Lotion

| | |
|---|---|
| (1) 1,3-butylene glycol | 6.0 |
| (2) Glycerin | 4.0 |
| (3) Oleyl alcohol | 0.1 |
| (4) POE(20) sorbitan monolaurate | 0.5 |
| (5) POE(15) lauryl alcohol ester | 0.5 |
| (6) Ethanol | 10.0 |
| (7) Filaggrin gene expression promoting agent of present invention: 3-(1'-piperidine) propionic acid | 1.0 |
| (8) Purified water | Balance |

Milky Lotion

| | |
|---|---|
| (1) Microcrystalline wax | 1.0 |
| (2) Beeswax | 2.0 |
| (3) Lanolin | 20.0 |
| (4) Liquid paraffin | 10.0 |
| (5) Squalane | 5.0 |
| (6) POE(20) sorbitan monooleate | 1.0 |
| (7) Propylene glycol | 7.0 |
| (8) Filaggrin gene expression promoting agent of present invention: 3-(1'-piperidine) propionic acid | 0.5 |
| (9) Filaggrin gene expression promoting agent of present invention: *Zanthoxylum* extract | 0.1 |
| (10) Sodium bisulfite | 0.01 |
| (11) Ethyl 4-hydroxybenzoate | 0.3 |
| (12) Fragrance | As suitable |
| (13) Purified water | Balance |

The invention claimed is:

1. A cosmetic method for promoting expression of filaggrin gene, comprising:
   administering a filaggrin gene expression promoting agent containing zanthoxylum extract and 3-(1'-piperidine)propionic acid, to a subject desiring promotion of the expression of the filaggrin gene.

2. The cosmetic method according to claim 1, wherein the filaggrin gene expression promoting agent consists essentially of zanthoxylum extract and 3-(1'-piperidine) propionic acid.

3. The cosmetic method according to claim 1, wherein the filaggrin gene expression promoting agent contains 0.1% zanthoxylum extract and 0.1% 3-(1'-piperidine) propionic acid.

4. The cosmetic method according to claim 1, wherein the subject further desires enhancing skin moisturizing.

5. The cosmetic method according to claim 4, wherein said administering results in enhancing of the skin moisturizing in the subject through enhancing the filaggrin gene expression in the subject.

6. The cosmetic method according to claim 1, wherein the subject further desires enhancing a skin barrier function.

7. The cosmetic method according to claim 1, wherein said administering results in enhancing of the skin barrier function in the subject through enhancing the filaggrin gene expression in the subject.

8. The cosmetic method according to claim 1, wherein the subject further desires enhancing skin moisturizing and skin barrier function.

9. The cosmetic method according to claim 1, wherein said administering results in enhancing of the skin barrier function in the subject through enhancing the filaggrin gene expression in the subject.

10. The cosmetic method according to claim 1, wherein said filaggrin gene expression promoting agent is administered to the subject at a time at which the biological rhythm of filaggrin gene expression level and the rhythm of the filaggrin gene expression level resulting from administration of the filaggrin gene expression promoting agent are synchronous.

11. The cosmetic method according to claim 2, wherein the subject further desires enhancing skin moisturizing.

12. The cosmetic method according to claim 11, wherein said administering results in enhancing of the skin moisturizing in the subject through enhancing the filaggrin gene expression in the subject.

13. The cosmetic method according to claim 2, wherein the subject further desires enhancing a skin barrier function.

14. The cosmetic method according to claim 13, wherein said administering results in enhancing of the skin barrier function in the subject through enhancing the filaggrin gene expression in the subject.

15. The cosmetic method according to claim 2, wherein the subject further desires enhancing skin moisturizing and skin barrier function.

16. The cosmetic method according to claim 15, wherein said administering results in enhancing of the skin barrier function in the subject through enhancing the filaggrin gene expression in the subject.

17. The cosmetic method according to claim 3, wherein the subject further desires enhancing skin moisturizing.

18. The cosmetic method according to claim 17, wherein said administering results in enhancing of the skin moisturizing in the subject through enhancing the filaggrin gene expression in the subject.

19. The cosmetic method according to claim 3, wherein the subject further desires enhancing a skin barrier function.

20. The cosmetic method according to claim 19, wherein said administering results in enhancing of the skin barrier function in the subject through enhancing the filaggrin gene expression in the subject.

* * * * *